United States Patent
Kumar et al.

(10) Patent No.: US 11,111,509 B2
(45) Date of Patent: Sep. 7, 2021

(54) BIO-ASSISTED PROCESS FOR CONVERSION OF MIXED VOLATILE FATTY ACIDS TO SELECTIVE DROP-IN FUELS

(71) Applicant: Indian Oil Corporation Limited, Mumbai (IN)

(72) Inventors: Manoj Kumar, Haryana (IN); Sandipam Srikanth, Haryana (IN); Dheer Singh, Haryana (IN); Suresh Kumar Puri, Haryana (IN); Sankara Sri Venkata Ramakumar, Haryana (IN)

(73) Assignee: Indian Oil Corporation Limited, Mumbai (IN)

( * ) Notice: Subject to any disclaimer, the term of this patent is extended or adjusted under 35 U.S.C. 154(b) by 107 days.

(21) Appl. No.: 16/353,666

(22) Filed: Mar. 14, 2019

(65) Prior Publication Data
US 2019/0284584 A1 Sep. 19, 2019

(30) Foreign Application Priority Data
Mar. 15, 2018 (IN) .............................. 201821009599

(51) Int. Cl.
| | | |
|---|---|---|
| *C12P 7/14* | (2006.01) | |
| *C10L 1/02* | (2006.01) | |
| *C12P 7/54* | (2006.01) | |
| *C12P 7/52* | (2006.01) | |
| *C12P 7/04* | (2006.01) | |
| *C12P 7/06* | (2006.01) | |
| *C12P 7/02* | (2006.01) | |
| *C25B 3/25* | (2021.01) | |
| *C25B 9/70* | (2021.01) | |
| *C25B 11/043* | (2021.01) | |

(52) U.S. Cl.
CPC .................. *C12P 7/14* (2013.01); *C10L 1/02* (2013.01); *C12P 7/02* (2013.01); *C12P 7/04* (2013.01); *C12P 7/065* (2013.01); *C12P 7/52* (2013.01); *C12P 7/54* (2013.01); *C25B 3/25* (2021.01); *C25B 9/70* (2021.01); *C25B 11/043* (2021.01); *C10L 2200/0484* (2013.01); *C10L 2290/26* (2013.01); *C10L 2290/38* (2013.01)

(58) Field of Classification Search
CPC .......... C25B 11/043; C25B 3/25; C25B 9/70; C10L 1/02; C10L 2200/0484; C10L 2290/26; C10L 2290/38; C12P 7/14; C12P 7/02; C12P 7/04; C12P 7/065; C12P 7/52; C12P 7/54
USPC ........................................................ 435/42
See application file for complete search history.

(56) References Cited

U.S. PATENT DOCUMENTS

| | | |
|---|---|---|
| 6,043,392 A | 3/2000 | Holtzapple et al. |
| 2011/0111475 A1 | 5/2011 | Kuhry et al. |
| 2012/0264184 A1 | 10/2012 | Ross et al. |
| 2013/0017590 A1 | 1/2013 | Chung et al. |
| 2014/0335586 A1 | 11/2014 | Zhang et al. |
| 2015/0251981 A1 | 9/2015 | Thevasahayam |

OTHER PUBLICATIONS

Weaver, Drop-in Fuels Are Road Ready, Oct. 30, 2020, Available online at: www.treehugger.com/drop-in-fuels-are-road-ready-85275.*

C. L. et al., "Water Splitting-Biosynthetic System with $CO_2$ Reduction Efficiencies Exceeding Photosynthesis", Bioenergy, vol. 352, Issue 6290, Jun. 3, 2016; http://science.sciencemag.org; 5 pages.

M. T. Agler, et al., "Chain Elongation with Reactor Microbiomes: Upgrading Dilute Ethanol to Medium-Chain Carboxylates", Energy & Environmental Science, vol. 5, 2012, pp. 8189-8192.

C. Urban, et al., "Production of Drop-In Fuel from Biomass at High Selectivity by Combined Microbial and Electrochemical Conversion", Energy & Environmental Science, vol. 10, 2017, 39 pages.

D. Vasudevan, et al., "Upgrading Dilute Ethanol from Syngas Fermentation to n-caproate with Reactor Microbiomes", Bioresource Technology, www.elsevier.com: vol. 151, 2014, pp. 378-382.

T.I.M Grootschollen, et al., "Two-Stage Medium Chain Fatty Acid (MCFA) Production from Municipal Solid Waste and Ethanol", Applied Energy, www.elsevier.com: vol. 116, 2014, pp. 223-229.

* cited by examiner

*Primary Examiner* — Jennifer M. H. Tichy
(74) *Attorney, Agent, or Firm* — Blank Rome LLP (57) ABSTRACT

The present invention relates to a two-stage process for production of drop-in fuels/alcohols (methanol, ethanol or butanol) from volatile fatty acids produced either synthetically from fossil resources or as metabolic intermediates in acidification step of anaerobic digestion process from waste biomass and organic materials.

11 Claims, 1 Drawing Sheet

Schematic representation of drop-in fuel production

BIO-ASSISTED PROCESS FOR CONVERSION OF MIXED VOLATILE FATTY ACIDS TO SELECTIVE DROP-IN FUELS

RELATED APPLICATION

This application claims the benefit of Indian Patent Application No. 201821009599, filed on Mar. 15, 2018. The content of that application is hereby incorporated by reference.

FIELD OF THE INVENTION

The present invention relates to bio-assisted process for conversion of mixed volatile fatty acids to selective drop-in fuels. More particularly, the present invention relates to a two phase bio-assisted reaction, mediated by a specific combination of electro-active bacteria, involving intensification and reduction of carboxylic acid in feedstock for production of drop-in fuels

BACKGROUND OF THE INVENTION

Oil refineries and coal-fired power plants are the leading anthropogenic source of $CO_2$ emission and are responsible for releasing over 9 billion metric tons of $CO_2$/year worldwide. Sustainable conversion of $CO_2$ to fuels and other value added chemical are of great importance in the current energy scenario. Natural photosynthesis harvests 130 TW of solar energy and generates up to 115 billion metric tons of biomass per year from the reduction of $CO_2$. The huge potential of this process motivates researchers to develop bio-mimetic systems that can convert $CO_2$ to value-added chemicals.

Volatile fatty acids (VFAs) are short-chain fatty acids including fatty acids from C2 to C6 (acetic, propionic, butyric, etc.) which are produced either synthetically from fossil resources or as metabolic intermediates in acidification step of anaerobic digestion process. Sustainably, VFAs could be obtained from various biodegradable organic wastes like kitchen waste, biomass waste, lignocellulosic agroindustrial wastes, sludge, etc., as key intermediates through dark fermentation. Mostly VFAs are transformed to gaseous products but their conversion to drop-in fuels is a value added process.

Various processes for biocatalytic conversion of $CO_2$ to multi-carbon compounds have been disclosed in the prior art. Certain microbiological processes have been shown to interact electrochemically with electrodes that are capable of shuttling electrons between the electrodes and the microorganisms.

US 20140335586 discloses a method for producing hydrocarbon fuels from biomass. This invention comprises of converting at least a portion of the biomass into medium-chain fatty acids or carboxylic acids ranging from C4 to C9 in the first stage followed by reacting at least a portion of the medium-chain fatty acids or carboxylic acids in a ketonization reactor to produce a ketonization product and finally reacting at least a portion of the ketonization product in a hydrodeoxygenation reactor to remove substantially all oxygen and produce a hydrodeoxygenation product comprising n-paraffins. This patent also describes about three different reactors required to carry out the said process. It is a 3 stage process involving the high energy consumption and requirement of catalysts for ketonization and hydrodeoxygenation. Major limitation of this process is catalyst recyclability and handling of secondary waste generated during the process along with the high energy consumption.

US 20110111475 discloses a method for producing hydrocarbon and hydrogen fuels and other products by a process employing a combination of fermentation and electrochemical stages. This inventions comprises of two stages where in the initial stage, the biomass is fermented with mixed culture derived the rumen contents of animal under anaerobic conditions for a sufficient time to produce VFAs. Further, these VFAs are subjected to electrolysis to convert them into hydrocarbons and hydrogen simultaneously. The stage 2 of this process is highly cost intensive and also needs a catalyst electrode to reduce the VFAs to hydrocarbons.

US 20130017590 discloses a method of preparing paraffins for transportation fuel or lubricating base oil using biomass in 3 stages. This invention comprised of preparing C2-C7 VFAs or their salts by fermentation of biomass followed by producing a mixture of C3-C13 ketones from VFAs or their salts and converting the ketone mixture into paraffins in the presence of a hydrogenation catalyst. This invention is also highly energy intensive and needs different catalysts for different stages generating huge quantities of secondary waste making the process non-sustainable. Recyclability of the catalyst is again a major issue.

U.S. Pat. No. 6,043,392 discloses a process for converting salts of volatile fatty acids, produced by anaerobic fermentation of biomass, into liquid fuels. This invention comprises of method for thermally converting VFAs salts to ketones by mixing dry calcium salts of VFAs with hot heat transfer agent in an evacuated container, thereby causing thermal decomposition of the calcium salts of VFAs to form ketone-containing vapor and calcium carbonate followed by separating the ketone-containing vapor from the calcium carbonate and heat transfer agent by condensing a mixture of ketones from the ketone-containing vapor. This invention is also based on a 3 stage process where energy intensive and catalyst based chemical steps are involved making the process non-sustainable.

US 20120264184 discloses a method of producing alcohols, hydrocarbons, or both from biomass. This invention includes converting biomass into a carboxylic acid followed by reacting the carboxylic acids with an olefin to produce an ester and finally hydrogenolyzing the ester to produce alcohol. This process is also a similar 3 stage process, however, one of the claim is that the $2^{nd}$ and $3^{rd}$ steps can be carried out in single reactor. However, the whole process is energy intensive and catalyst dependent process generating secondary wastes.

US 20150251981 discloses a method for synthesizing alcohol at ambient conditions based on paramagnetic catalyst and fluctuating magnetic field. The invention comprising of contacting a carboxylic acid with water to form a first mixture followed by contacting the first mixture with a superparamagnetic catalyst to form a second mixture and finally exposing the second mixture to a fluctuating magnetic field to form a third mixture thereby yielding the alcohol.

Research article entitled "Water splitting-biosynthetic system with $CO_2$ reduction efficiencies exceeding photosynthesis" (Liu C, Colón BC, Ziesack M, Silver PA, Nocera DG, Science, 2016, 352(6290), 1210-1213) describes about the development of hybrid water splitting biosynthetic system based on a biocompatible inorganic catalyst system (Co-p/Co-Pi) to split water into molecular hydrogen and oxygen at low driving voltages. When grown in contact with these catalysts, *Ralstonia eutropha* consumed the produced $H_2$ to synthesize biomass and fuels or chemical products from low $CO_2$ concentration in the presence of $O_2$. They proposed that, coupling this hybrid device to existing photovoltaic systems would yield a $CO_2$ reduction energy efficiency of ~10%, exceeding that of natural photosynthetic systems based on calculations. However, they didn't check this practically and using a single culture is not very practical when waste gases are considered as substrates. Moreover, they tried only with $CO_2$ but not with waste organics, which can be a more abundant carbon source.

Research article titled "Upgrading dilute ethanol from syngas fermentation to n-caproate with reactor microbiomes" (Vasudevan D et al, Bioresource Technology 151 (2014) 378-382) describes a proof of concept for the bio-processing system with diluted ethanol and acetic acid in actual syngas fermentation effluent as the substrate for chain elongation into n-caproic acid using open cultures of microbial populations (reactor microbiomes). About 1 g/l of n-caproic acid was produced at pH 5.44 and higher butyrate production rate (20 g/l/day) was proposed to be impacting negative on further production of n-Caproate. Limitation of this process is low production rates, which cannot meet the industrial scale-up.

Research article entitled "Two-stage medium chain fatty acid (MCFA) production from municipal solid waste and ethanol" (Grootscholten et al, Applied Energy 116 (2014) 223-229) describes a two-stage process for the conversion of organic fraction of municipal solid waste (OFMSW) into medium chain fatty acids (MCFAs) in presence of ethanol. The obtained caproate concentrations were above the solubility of caproic acid in water. They proposed that, separating the chain elongation and hydrolysis steps can be a good option for easier control of competitive processes by controlling the carbon dioxide addition and the hydrogen partial pressure. Main limitation of this process lies in the two stage approach, where the energy input will be more and also it was observed during the study that occasionally, MCFA production was lowered by substantial butyrate production. Addition of ethanol is also adds to the operational cost to achieve the MCFA production. Instead, converting the butyrate to butanol will have more advantage, which we demonstrated in our invention.

Research article entitled "Chain elongation with reactor microbiomes: upgrading dilute ethanol to medium-chain carboxylates" (Agler et al, Energy & Environmental Science, 2012, 5, 8189) also describes a similar method for chain elongation of VFAs in presence of ethanol and produced n-caproic acid, a 6-carbon-chain carboxylic acid. In-line product extraction was also achieved at a rate exceeding 2 g/l. Main limitation of this process also lies in the requirement of ethanol as electron donor.

Research article entitled "Production of drop-in fuel from 1 biomass at high selectivity by combined microbial and electrochemical conversion" (Urban et al, Energy Environ. Sci., 2017, 10, 2231) discloses a proof-of-concept for the production of MCFA (mainly n-caproic and n-caprylic acid) during continuous fermentation from corn beer and corn silage followed by their separation through pertraction and then electrochemical conversion to hydrocarbons via Kolbe reaction and other reaction pathways. The major limitation of this process is it involves 3 stages, where the 2 & 3 stages are highly energy intensive. Membranes and cartridges for the pertraction step needs to be replaced at regular time intervals.

Therefore, there is a need in the art to provide an efficient process for production of drop-in fuels through a bio-assisted process.

SUMMARY OF THE INVENTION

The present disclosure relates to a bio-assisted process for production of drop-in fuels from $CO_2$ and volatile fatty acid rich source, said process comprising:
(a) providing a first electrochemical system comprising at least one working electrode, at least one counter electrode, and a medium inoculated with selectively enriched electro-active bacteria selected from the group consisting of *Geobacter anodireducens, Clostridium ljungdahlii, Acetobacterium woodii, Sporomusa acidovorans, Propionibacterium acidifaciens, Acetobacterium carbinolicum, Pseudomonas stutzeri* (MTCC 25027), *Pseudomonas fragi* (MTCC 25025), *Pseudomonas aeruginosa* (MTCC 5389), Psuedomonas *alcaligenes, Schewanella putrefaciens, Clostridium aciditolerans. Enterobacter aerogenes* (MTCC 25016), *Shewanella* sp. (MTCC 25020), and combinations thereof;
(b) providing feedstock to the first electrochemical system of step (a), wherein the feedstock comprises $CO_2$ with or without the volatile fatty acid rich source;
(c) intensifying carboxylic acids in the feedstock of step (b) to obtain an effluent comprising intensified carboxylic acids;
(d) providing a second electrochemical system comprising at least one working electrode, at least one counter electrode, and a medium inoculated with selectively enriched electro-active bacteria selected from the group consisting of *Sporomusa ovate, Clostridium acetobutylicum, Clostridium butyricum, Clostridium acidurici, Pseudomonas aeruginosa* (MTCC 5388), *Pseudomonas putida* (MTCC 5387), *Clostridium carboxidivorans, Clostridium beijerinckii, Schewanella oneidensis, Geobacter sulfurreducens, Clostridium cellulolyticum, Clostridium cellulosi, Clostridium cellulovorans, Alicaligens* sp. (MTCC 25022), *Serratia* sp. (MTCC 25017), *Lysinibacillus* sp. (MTCC 5666), and combinations thereof; and
(e) reducing the intensified carboxylic acids of step (c) in the second electrochemical system to obtain the drop-in fuels;
wherein the working electrode of the first electrochemical system is composed of a material selected from the group consisting of graphite plate, carbon brush, carbon paper, graphite felt, activated carbon cloth, and combinations thereof;
wherein the counter electrode of the first electrochemical system is modified with a material selected from the group consisting of CNT, graphene, charcoal, activated carbon, SS mesh, nickel oxide, zinc oxide, and iron oxide;
wherein the volatile fatty acid rich source comprises at least 0.5% formic acid, provided that if the formic acid is not already present in the feedstock the feedstock is supplemented with at least 0.5% formic acid;
wherein the working electrode of the second electrochemical system is composed of a material selected from the group consisting of graphite plate, graphite rod, carbon brush, carbon paper, carbon plate, graphite felt, activated carbon cloth, and combinations thereof; and
wherein the counter electrode of the second electrochemical system is modified with a material selected from the group consisting of CNT, $Co_9S_8$, graphene, FTO/NiO, Ni/Fe layered double hydroxide, Si/TiO$_2$ nanowires, charcoal, activated carbon, nickel oxide, zinc oxide, and iron oxide.

DETAILED DESCRIPTION OF THE INVENTION

Figure 1:
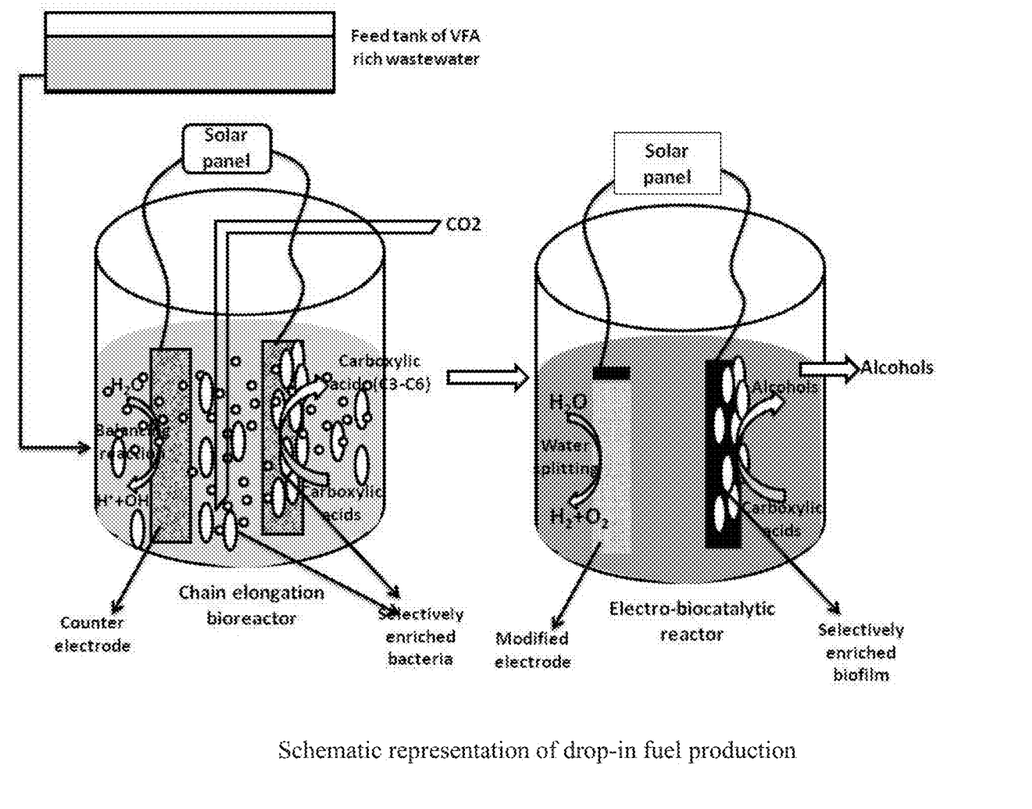
FIG. 1 illustrates a schematic representation of drop-in fuel production.

The present invention discloses a two-stage process for production of drop-in fuels/alcohols from volatile fatty acids produced either synthetically from fossil resources or as metabolic intermediates in acidification step of anaerobic digestion process from waste biomass and organic materials.

The present invention also discloses a sustainable two stage process wherein any VFA source, having diverse combination of carboxylic acids, can be used as feedstock/starting material. In the first stage, intensification of specific carboxylic acids having chain length between C2 and C6 is carried out in presence of CO$_2$ in an electro-assisted fermentation process. In stage-2, the intensified carboxylic acids obtained at the end of Stage 1 are reduced to specific alcohols/drop-in fuels through bio-electrochemical approaches using the in situ generated energy/hydrogen.

Both the reactors in stage 1 and 2 are equipped with two electrodes and inoculated with selectively enriched electroactive bacteria. The reactor for stage-1 is single chambered and can be operated in batch or continuous or semi-continuous mode in continuous stirred tank reactor (CSTR) or up-flow anaerobic sludge blanket reactor (UASB) or plug-flow reactor or sequential batch reactor (SBR). The structure of the reactor for stage-1, specifically its single chambered arrangement presents numerous advantages. For instance, in a single chambered reactor, both the electrodes are kept in the same chamber, which eliminates the requirement of an expensive membrane. This structure allows the present reaction to be more cost-efficient over other processes which have been available in the art.

One of the electrodes in the reactors of stage-1 is for oxidation reaction. In an embodiment, the said electrode can be made of graphite plate, carbon brush, carbon paper, graphite felt, and activated carbon cloth (ACC), and combinations thereof. The other electrode is meant for reduction which is a modified electrode with higher redox potentials. The modification can be done using any electrically conductive and bio-compatible support materials, including but not limited to, CNT, graphene, charcoal, activated carbon, metal oxides of nickel or zinc or iron, etc.

The energy required for carrying out the reaction can be supplied from any renewable source like solar or wind or geo-thermal or grid etc The feedstock for reactor in stage 1 can be CO$_2$ alone or VFA rich leachate along with CO$_2$ as C-source. The VFA can be obtained from different sources, viz., kitchen waste, biomass waste, agricultural waste, municipal waste (biodegradable), lignocellulosic waste, de-oiled algal cake, etc., with only one clause that it should contain 0.5% formic acid or else to be amended. The CO$_2$ can be purified or also can be obtained from off-gases of power plants, industries, etc.

The reactor in stage-1 should be inoculated with selectively enriched bacteria of different groups viz., electroactive bacteria (EAB), chemoautotrophic bacteria, homoacetogenic bacteria and acid producing bacteria (APB), which can work alone or in combination with each other. Bacteria that can be used in the present inventions include but not limited to *Geobacter anodireducens, Clostridium ljungdahlii, Acetobacterium woodii, Sporomusa acidovorans, Propionibacterium acidifaciens, Acetobacterium carbinolicum, Pseudomonas stutzeri* MTCC 25027 deposited on Apr. 20, 2015 at Microbial Type Culture Collection (MTCC), Institute of Microbial Technology, Shanti Path, 39A, Sector 39, Chandigarh, 160036, India, *Pseudomonas fragi* MTCC 25025 deposited on Apr. 10, 2015, *Pseudomonas aeruginosa* MTCC 5389 deposited on Dec. 17, 2007, *Schewanella putrefaciens, Clostridium aciditolerans, Enterobacter aerogenes* MTCC 25016 deposited on Apr. 9, 2015, *Shewanella* sp. MTCC 25020 deposited on Apr. 9, 2015.

Other bacteria which can work alone or in combination with each other includes but not limited to: Geobacter anodireducens, *G. argillaceus, G. bemidjiensis, G. bremensis, G. chapellei, G. daltonii. G. grbiciae, G. hydrogenophilus, G. lovleyi, G. luticola, G. metallireducens, G. pelophilus, G. pickeringit, G. psychrophilus, G. soh, G. sulirreducens, G. thiogenes, G. toluenoxydans. G. uranireducens, Schewanella abyssi, S. aestuarii, S. algae, S. algidipiscicola, S. amazonensis, S. aquimarina, S. arctica, S. atlantica, S. baltica, S. basaltis, S. benthica, S. Canadensis, S. chilikensis, S. colwelliana, S. corallii, S. decolorationis, S. denitrificans, S. dokdonensis, S. donghaensis, S. fidelis, S. fodinae, S. frigidimarina S. gaetbuli, S. gelidimarina, S. glacialipiscicola, S. hafniensis, S. halfaxensis, S. halitosis, S. hanedai, S. indica, S. irciniae, S. japonica, S. kaireitica, S. htorisediminis, S. livingstonensis, S. loihica. S. mangrove, S. marina, S. marinintestina, S. marisflavi, S. morhuae, S. olleyana, S. oneidensis, S. piezotolerans, S. pacifica, S. pealeana, S. piezotolerans, S. pneumatophori, S. profinda, S. psychrophila, S. putrefaciens, S. sairae, S. schegeliana, S. sediminis, S. seohaensis, S. spongiae, S. surugensis, S. upenei, S. vesiculosa, S. violacea, S. waksmanii, S. woodyi, S. xiamenensis, Pseudomonas aeruginosa, P. alcaligenes, P. anguilliseptica, P. argentntensis, P. borbori, P. citronellolis, P. flavescens, P. mendocina, P. nitroreducens, P. oleovorans, P. pseudoalcaligenes, P. resinovorans, P. straminea, P. balearica, P. luteola, P. stutzeri, Sporomusa ovate, Clostridium ljungdahlii, Acetobacterium bakii, Acetobacterium carbinolicum, Acetobacterium fimetarium, Acetobacterium malicum, Acetobacterium paludpsum, Acetobacterium tundra, Acetobacterium wieringae, Acetobacterium woodii, Sporomusa acidovorans, cyanobacterium Synechocystis, Pelotomaculum thermopropionicum, Megasphaera hexanoica, Megasphaera hominis, Megasphaera cerevisiae, Megasphaera elsdenii, Megasphaera micronuciformis, Megasphaera paucivorans, Megasphaera sueciensis, M. cerevisiae, Anaeroglobus geminates, Bacillus subtilis, Propionibacterium acidifaciens, Propionibacterium acidipropionici, Propionibacterium acnes Propionibacterium australense, Propionibacterium avidum, Propionibacterium cyclohexanicum, Propionibacterium damnosum, Propionibacterium freudenreichii, Propionibacterium granulosum, Propionibacterium jensenii, Propionibacterium lymphophilum, Propionibacterium microaerophilu, Propionibacterium namnetense, Propionibacterium olivae, Propionibacterium propionicus, Propionibacterium thoenii*, etc.

In an embodiment, the reactor in stage-1 can be operated at temperatures ranging from 20-50° C. In another embodiment, the reactor in stage-1 can be operated at pH ranging between 6.5 to 9.0.

In yet another embodiment, the reactor in stage-1 can be operated under the applied potential in the range of 1-4 V or applied current anywhere in the range of 30-150 A/m$^2$ vs Ag/AgCl reference electrode. In accordance with the present invention, reactor in stage-1 can be operated in batch mode with a hydraulic retention time (HRT) of 24-72 h or in continuous mode with 18-48 h HRT.

Subsequently, the effluent from reactor in stage-1 enriched with specific type of VFAs is supplied to the reactor in stage-2, where it is converted to alcohols. The chain length of the alcohol depends on the availability of $H_2/H^+$ in the reactor. In presence of the in situ generated $H_2/H^+$, the chain length of dominant alcohol of the total product remains same as the VFA obtained in stage-1 but it shortens by 1 carbon when the source of $H_2/H^-$ is absent in the reactor.

The reactor in stage-2 can be single chambered or double chambered operating in batch or continuous or semi-continuous mode in continuous stirred tank reactor (CSTR) or up-flow anaerobic sludge blanket reactor (UASB) or plug-flow reactor or sequential batch reactor (SBR). In double chambered configuration, the membrane used to separate the 2 chambers can be proton exchange membrane (PEM) or cation exchange membrane (CEM) or porcelain disk with micro pores.

Similar to stage-1, one of the electrodes in reactor of stage-2 also meant for oxidation. It should be modified for getting higher oxidation potentials in case of generating $H_2/H^+$ in situ in the reactor itself or else, the modification is not required. The electrode can be made of different materials viz., graphite plate, carbon brush, carbon paper, graphite felt, activated carbon cloth (ACC), etc., and the modification can be done using metal oxides of zirconium, cadmium nickel, zinc, iron, cobalt, titanium, silicone and their alloy, their phosphorous and sulfur composites etc. The other electrode is meant for reduction which is a carbon graphite electrode modified for obtaining higher redox potentials. The modification can be done using highly conductive materials like CNT, graphene, charcoal, activated carbon, etc.

The energy required for carrying out the reaction can be supplied from any renewable source like solar or wind or geo-thermal or grid etc. The effluent from reactor in stage-1 acts as feedstock for the reactor in stage 2.

The reactor in stage-2 also should be inoculated with selectively enriched biocatalyst and have the combination of different bacterial groups, viz., electro-active bacteria (EAB), sulfate-reducing bacteria, homoacetogenic bacteria and metal reducing bacteria, which can work in synergistic interaction with each other. Bacteria that can be used in the present inventions include but not limited to Sporomusa ovate, *Clostridium acetobutylicum, Clostridium butyricum, Clostridium acidurici, Pseudomonas aeruginosa* MTCC 5388 deposited on Dec. 17, 2007, *Pseudomonas putida* MTCC 5387 deposited on Dec. 17, 2007, *Clostridium carboxidivorans, Clostridium beijerinckii, Schewanella oneidensis, Geobacter sulfurreducens, Clostridium cellulolyticum, Clostridium cellulosi, Clostridium cellulovorans, Alicaligens* sp. MTCC 25022 deposited on Apr. 10, 2015, *Serratia* sp. MTCC 25017 deposited on Apr. 9, 2015, *Lysinibacillus* sp. MTCC 5666 deposited on Oct. 12, 2011, and combinations thereof.

Other bacteria which can work alone or in combination with each other includes but not limited to: *Geobacter anodireducens, G. argillaceus, G. bemidjiensis, G. bremensis, G. chapellei. G. daltonii, G. grbiciae, G. suifirreducens, G. thiogenes, G. toluenoxydans, G. uraniireducens, Schewanella abyssi, S. aestuarii, S. algae. S. algidipiscicola, S. amazonensis, S. aquimarina, S. arclica, S. litorisediminis, S livingslonensis, S. loihica, S mangrove, S. marina, S. marin-intestina, S. marisfavi, S. morhuae, S. olleyana, S. oneidensis. S. piezotolerans, S. pacifica, S. pealeana, S. piezotolerans, S. pneumatophori, S. profunda, S. psychrophila, S. putrefaciens, S. sairae, S. schegeliana, S. sediminis, S. seohaensis, S. spongiae, S. surugensis, S. upenei, S. vesiculosa, S. violacea, S. waksmanii, S. woodyi, S. xiamenensis, Pseudomonas aeruginosa, P. alcaligenes, P. anguilliseptica, P. argentinensis, P. borbori, P. citronellolis, P. flavescens, P. mendocina, P. nitroreducens, P. oleovorans, P. pseudoalcaligenes, P. resinovorans, P. straminea, P. balearica, P. luteola, P. stutzeri, Sporomusa ovate, Clostridium ljungdahlii, Sporomusa acidovorans,* cyanobacterium *Synechocystis, Pelotomaculum thermopropionicum, Megasphaera hexanoica, Megasphaera hominis, Megasphaera cerevisiae, Megasphaera elsdeni, Megasphaera micronuciformis Megasphaera paucivorans, Megasphaera sueciensis, M. cerevisiae, Anaeroglobus geminates, Clostridium acetobutylicum, Clostridium butyricum, Clostridium diolis, Clostridium beijerinckii, Clostridium acidisoli, Clostridium aciditolerais, Clostridium acidurici, Clostridium aerotolerans, Clostridium cadaveris, Clostridium caenicola, Clostridium caninithermale, Clostridium carboxidivorans, Clostridium carnis, Clostridium cavenidishii, Clostridium celatum, Clostridium celerecrescens, Clostridium cellobioparum, Clostridium cellofermentans, Clostridium cellulolyticun, Clostridium celhdlosi, Clostridium cellulovorans, D. acrylicus, D. aerotolerans, D. aespoeensis, D. africanus, D. alaskensis, D. alcoholivorans, D. alkalitolerans, D. aminophilus, D. arcticus, D. baarsii, D. baculatus, D. baslinii, D. biadhensis, D. bizertensis, D. burkinensis, D. butratiphilus, D. capillatus, D. carbinolicus, D. carbinoliphilus, D. cuneatus, D. dechloracetivorans, D. desulfuricans, D. ferrireducens, D. frigidus, D. fructosivorans, D. furfurals, D. gabonensis, D. giganteus, D. gigas, D. gracilis, D. halophilus, D. hydrothermalis, D. idahonensis, D. indonesiensis, D. inopinatus, D. intestinalis, D. legalli, D. alitoralis, D. longreachensis, D. longus, D. magneticus, D. marinus, D. marinisediminis, D. marrakechensis, D. mexicamis, D. multispirans, D. oceani, D. oxamicus, D. oxyclinae, D. paquesii, D. piezophilus, D. pigra, D. portus, D. profindus, D. psychrotolerats, D. putealis, D. salixigens, D. sapovorans, D. senezii, D. simplex, D. sulfodismutans, D. termitidis, D. thermophilus, D. tunisiensis, D. vietnamensis, D. vulgaris, D. zosterae, Klebsiella granulomatis, Klebsiella oxytoca, Klebsiella pneumonia, Klebsiella terrigena, Klebsiella varitcola, Bacillus subtilis, Zvmomonas mobilis, Zymomonas* anaerobia etc.

An embodiment of the present invention provides a bio-assisted process for production of drop-in fuels from $CO_2$ and volatile fatty acid rich source, said process comprising:

(a) providing a first electrochemical system comprising at least one working electrode, at least one counter electrode, and a medium inoculated with selectively enriched electro-active bacteria selected from the group consisting of Geobacter anodireducens, *Clostridium ljungdahlii, Acetobacterium woodii, Sporomusa acidovorans, Propionibacterium acidifaciens, Acetobacterium carbinolicum, Pseudomonas stutzeri* (MTCC 25027), *Pseudomonas fragi* (MTCC 25025), *Pseudomonas aeruginosa* (MTCC 5389), *Psuedomonas alcaligenes, Schewanella putrefaciens, Clostridium aciditolerans, Enterobacter aerogenes* (MTCC 25016), *Shewanella* sp. (MTCC 25020), and combinations thereof;

(b) providing feedstock to the first electrochemical system of step (a), wherein the feedstock comprises $CO_2$ with or without the volatile fatty acid rich source;

(c) intensifying carboxylic acids in the feedstock of step (b) to obtain an effluent comprising intensified carboxylic acids;

(d) providing a second electrochemical system comprising at least one working electrode, at least one counter electrode, and a medium inoculated with selectively enriched electro-active bacteria selected from the group consisting of Sporomusa ovate, *Clostridium acetobulicum*, *Clostridium butyricum*, *Clostridium acidurici*, *Pseudomonas aeruginosa* (MTCC 5388), *Pseudomonas putida* (MTCC 5387), *Clostridium carboxidivorans*, *Clostridium beijerinckii*, *Schewanella oneidensis*, *Geobacter sulfurreducens*, *Clostridium cellulolyticum*, *Clostridium cellulosi*, *Clostridium cellulovorans*, *Alicaligens* sp. (MTCC 25022), *Serratia* sp. (MTCC 25017), *Lysinibacillus* sp. (MTCC 5666), and combinations thereof; and (e) reducing the intensified carboxylic acids of step (c) in the second electrochemical system to obtain the drop-in fuels;

wherein the working electrode of the first electrochemical system is composed of a material selected from the group consisting of graphite plate, carbon brush, carbon paper, graphite felt, activated carbon cloth, and combinations thereof; wherein the counter electrode of the first electrochemical system is modified with a material selected from the group consisting of CNT, graphene, charcoal, activated carbon, SS mesh, nickel oxide, zinc oxide, and iron oxide;

wherein the volatile fatty acid rich source comprises at least 0.5% formic acid, provided that if the formic acid is not already present in the feedstock the feedstock is supplemented with at least 0.5% formic acid;

wherein the working electrode of the second electrochemical system is composed of a material selected from the group consisting of graphite plate, graphite rod, carbon brush, carbon paper, carbon plate, graphite felt, activated carbon cloth, and combinations thereof; and wherein the counter electrode of the second electrochemical system is modified with a material selected from the group consisting of CNT, $Co_9S_8$, graphene, FTO/NiO, Ni/Fe layered double hydroxide, $Si/TiO_2$ nanowires, charcoal, activated carbon, nickel oxide, zinc oxide, and iron oxide.

In another embodiment of the present invention, the first electrochemical system is operated at a temperature ranging from 20° C. to 50° C.

In yet another embodiment of the present invention, the first electrochemical system is operated at a pH ranging from 6.5 to 9.0.

In still another embodiment of the present invention, the first electrochemical system is operated at an applied potential ranging from 1 V to 4 V.

In a further embodiment of the present invention, the working electrode of the second electrochemical system is modified with a material selected from the group consisting of CNT, graphene, activated charcoal, noble metal, composite of Zr or Ti or Cd or Fe, metal-free alloy, metal carbide, phosphide, and nickel oxide, zinc oxide, iron oxide, metal-phosphorous alloy, metal-sulfur alloy, metal organic framework, and combinations thereof.

Yet another embodiment of the present invention provides that the carboxylic acid in step (c) has a length ranging from C2 to C6.

Still another embodiment of the present invention provides that the second electrochemical system is operated at a temperature ranging from 20° C. to 50° C.

A further embodiment of the present invention provides that the second electrochemical system is operated at a pH ranging from 4.0 to 6.0.

Another embodiment of the present invention provides that the second electrochemical system is operated at an applied potential ranging from 2 V to 6 V.

In another embodiment of the present invention, there is provided that the volatile fatty acid rich source is selected from the group consisting of kitchen waste, biomass waste, agricultural waste, biodegradable municipal waste, lignocellulosic waste, and de-oiled algal cake.

In yet another embodiment of the present invention, there is provided that the reduction of carboxylic acids in step (e) is carried out in presence of a redox shuttler selected from the group consisting of neutral red, methylene blue, phenazine derivative, iron based metal complex, nickel based metal complex, zinc based metal complex, AQDS, and combinations thereof.

In a further embodiment of the present invention, the drop-in fuels are selected from the group consisting of methanol, ethanol, butanol, formic acid, acetic acid, propanoic acid, butanoic acid, valeric acid, and caproic acid.

During stage-2, redox shuttlers such as, neutral red (NR), methylene blue (MB), phenazine derivatives, iron/nickel/zinc based metal complexes, etc., can be added individually or in combinations to enhance the electron exchange between the electrode and biocatalyst. In an embodiment, the reactor in stage-2 can be operated at temperatures ranging from 20-50° C. In an embodiment, the reactor in stage-2 can be operated at pH ranging between 4.0 and 6.0. The reactor in stage-1 can be operated under applied potential in the range of 2-6 V or applied current anywhere in the range of 100-250 $A/m^2$ vs Ag/AgCl reference electrode.

The reactor in stage-2 can be operated in batch mode or in continuous mode with a hydraulic retention time (HRT) of 24-72.

Having described the basic aspects of the present invention, the following non-limiting examples illustrate specific embodiment thereof.

EXAMPLES

Example 1: General Example

Experiments were carried out in 2 stages, where the intensification of specific VFA was done during stage-1 followed by the VFA reduction to alcohol in stage-2. The existing fermentors were modified by inserting a pair of electrodes (total/working volume, 2.8/2.0 L) and used for this study in both the stage-1 and stage-2. For stage-1 operation, the bioreactor was inserted with graphite rod wrapped with ACC as electrode for oxidation and carbon powder coated graphite rod wrapped with SS mesh as electrode for reduction. Both the electrodes were connected to potentiostat through SS wires and an applied cell potential of +2V was applied to the circuit against Ag/AgCl (3M KCL) reference electrode during stage-1 operation. The current consumption during operation was monitored using chronoamperometry (CA). $CO_2$ alone or along with VFA rich organic waste leachate was used as substrate for stage-1 operation in batch and continuous modes with a retention time of 72 h and 24 h respectively, at pH 6.5±0.1. Trace metal solution was also added to the reactor, when $CO_2$ alone was used as substrate to support the microbial activity. Constant mixing was provided to the bioreactor at a rate of 500 rpm experiments were carried out at ambient conditions. Samples were collected at regular time intervals and analyzed for VFAs using gas chromatography at regular time intervals.

During stage-2 operation the effluent from stage-1, enriched with specific VFA was used as substrate and converted those VFAs into alcohols. For this, two approaches were followed, where in approach-1 modified electrode for oxidation was used to generate $H_2/H^+$ in situ in the reactor and in approach-2, non-modified electrode for oxidation was used. In approach-1, the bioreactor was inserted with graphite rod modified with ZrTi—P as electrode for oxidation and carbon felt and activated carbon filled in cylinder made of SS mesh as electrode for reduction. In approach-2, the electrode for oxidation is replaced with graphite rod wrapped with ACC, keeping the rest as same to approach-1. In both the cases, the electrodes were connected to potentiostat through SS wire and +3V of cell potential was applied to the circuit against Ag/AgCl (3M KCL) reference electrode. NR (0.0001%) was added as redox shuttler in stage-2 bioreactor to facilitate electron exchange between the biocatalyst and electrode. The current consumption during operation was monitored using chronoamperometry (CA). The effluent from stage-1 was used as feedstock for both the approaches of stage-2, after adjusting the pH to 5.0±0.1 and the same was maintained throughout operation. The pH was maintained using a combination of Acid ($H_3PO_4$)/Base (NaOH). Mixing was provided at a rate of 500 rpm and experiments were carried out at ambient conditions with HRT of 72 h and 24 h during batch and continuous mode operations respectively. Samples were collected at regular time intervals and analyzed for alcohols production using gas chromatography at regular time intervals.

Example 2: Using C02 as Sole C-Source

In one of the examples, the experiment was carried out using $CO_2$ alone as C-source at a rate of 15 ml/min for 72h of HRT and formic acid (0.5%) as proton source in stage-1. For the reaction, basic media containing $NH_4Cl$ of 500 mg/L, $MgCl_2.6H_2O$ of 160 mg/L, Peptone 250 mg/L Yeast Extract of 26 mg/L along with the trace elements solution (per litre, Nitrilotriacetic acid, 1.5 g; $MgSO_4 \times 7H_2O$, 2.0 g; $MnSO_4 \times H_2O$, 1.5 g; NaCl, 1.0 g; $FeSO_4 \times 7H_2O$, 0.1 g; $CoSO_4 \times 7H_2O$, 0.134 g; $CaCl_2) \times 2H_2O$, 0.1 g; $ZnSO_4 \times 7H_2O$, 0.18 g; $CuSO_4 \times 5H_2O$, 0.01 g; $KAl(SO_4)_2 \times 12H_2O$, 0.02 g; $H_3BO_3$, 0.01 g; $Na_2MoO_4 \times 2H_2O$, 0.01 g; $NiCl_2 \times 6H_2O$, 0.03 g; $Na_2SeO_3 \times 5H_2O$, 0.50 mg) and vitamin solution (per litre, biotin, 2 mg; pantothenic acid, 5 mg; B-12, 0.1 mg; p-aminobenzoic acid, 0.25 mg; thioctic acid (alpha lipoic), 5 mg; nicotinic acid, 5 mg; thiamine, 5 mg, riboflavin, 5 mg; pyridoxine HCl, 10 mg, folic acid, 2 mg) was used.

Rest of the operating conditions was maintained as given in experimental conditions. The combination of *Enterobacter aerogenes* MTCC 25016, *Shewanella* sp. MTCC 25020, *Pseudomonas stutzferi* MTCC 25027, *Pseudomonas aeruginosa* MTCC 5389 was used as biocatalyst during stage-1. The current consumption on CA during stage-1 started increasing with time and in 6h of operation, it reached 4.1±1.6 A/m2 and sustained afterwards at similar value till 72 h of operation. Results showed enrichment of acetic acid (9.2 g/l) from $CO_2$ along with formic acid (4.2 g/l) during stage-1 (Table 1).

The effluent from stage-1 operation enriched with acetic acid was used as substrate for stage-2 and no other C-source was provided. The combination of *Clostridium butyricum, Serratia* sp. MTCC 25017, *Pseudomonas aeruginosa* MTCC 5388, *Pseudomonas putida* MTCC 5387, was used as biocatalyst during stage-2. During approaches of stage-2, the current consumption started immediately but reached to a maximum of 8.2±2.1 A/m2 in approach-1, where the in situ H2/H+ generation takes place on the modified electrode, while the current consumption restricted to 2.3±0.6 A/m$^2$ only in approach-2. Transformation of acetic acid to alcohol was observed during both the approaches of stage-2 but approach-1 resulted in the dominant production of ethanol (6.7 g/l), while the approach-2 produced methanol (5.72). The in situ generated $H_2/H^+$ along with the formic acid supported the reduction of acetic acid to ethanol without reduction in carbon chain, while in the approach-2, formic acid alone along with the electrode potential supported the transformation which resulted in loss of carbon producing methanol. The CCE for stage-1 is about 26% due to issues in $CO_2$ solubility. During stage-2, about 92% CCE was recorded during approach-1 but the CCE was about 54% only during approach-2 due to the non-availability of $H_2/H^+$ in the reactor resulting in the loss of carbon as $CO_2$.

TABLE 1

Two stage operation of bioreactor in batch mode using $CO_2$ as C-source

|  | Influent VFA (g/l) | Effluent VFA after stage-1 (g/l) | Stage-2/ approach-1, Product formed (g/l) | Stage-2/ approach-2, Product formed (g/l) |
|---|---|---|---|---|
| Methanol | 0 | 0 | 0.81 | 5.72 |
| Ethanol | 0 | 0 | 6.7 | 0.22 |
| Butanol | 0 | 0 | 0 | 0 |
| Formic acid | 5 | 4.2 | 0.021 | 0.02 |
| Acetic acid | 0 | 9.2 | 0.87 | 0.87 |
| Propanoic acid | 0 | 0 | 0 | 0.00 |
| Butanoic acid | 0 | 0 | 0.49 | 0.00 |
| Total | 0 | 13.4 | 8.89 | 6.83 |

Example 3: Leachate from Kitchen Waste Along with C02 as C-Source

In another example, the experiment was carried out using leachate from kitchen waste (VFA: 28.24 g/l; TOC: 34.61 g/l) along with $CO_2$ as C-source (15 ml/min) and formic acid was maintained at 0.5% by external addition of required quantity. The combination of *Clostridium ljungdahlii, Enterobacter aerogenes* MTCC 25016, *Pseudomonas fragi* MTCC 25025, *Pseudomonas stutzferi* MTCC 25027 was used as biocatalyst during stage-1. Here also, the current consumption during stage-1 was observed to be increasing with time and in 3 h of operation, it reached 6.1±0.8 A/m$^2$ and sustained afterwards at similar range till 72 h of operation. Results showed the intensification of acetic acid (13.78 g/l) and butyric acids (11.96 g/l) during stage-1 at the expense of other constituents of leachate and $CO_2$ (Table 2).

The effluent from stage-1 operation was made as substrate for stage-2 of both the approaches and no other C-source was provided for stage-2 operation. Rest of the operating conditions remained same. The combination of *Pseudomonas putida* MTCC 5387, *Clostridium acetobutylicum*, *Clostridium beijerinckii*, *Serratia* sp. MTCC 25017 was used as biocatalyst during stage-2. Similar to the example-1, the current consumption on CA started immediately after start-up during both the approaches of stage-2 and showed a maximum value of $10.2 \pm 0.55$ A/m$^2$ and $1.6 \pm 0.85$ A/m$^2$ respectively for approach-1 and approach-2. Alcohol production was observed during both the approaches of stage-2 but approach-1 resulted in the dominant production of butanol (11.08 g/l) and ethanol (10.68 g/l), while the approach-2 produced methanol (18.7 g/l). In situ generation of H2/H+ is the major reason behind the variation in alcohol composition. The CCE for stage-1 is about 48%. During stage-2, about 93% CCE was recorded during approach-1 but the CCE was only 50% during approach-2 due to the non-availability of $H_2/H^+$ in the reactor resulting in the loss of carbon as $CO_2$.

TABLE 2

Two stage operation of bioreactor in batch mode using kitchen waste leachate along with $CO_2$ as C-source

|  | Influent VFA (g/l) | Effluent VFA after stage-1 (g/l) | Stage-2/ approach-1, Product formed (g/l) | Stage-2/ approach-2, Product formed (g/l) |
| --- | --- | --- | --- | --- |
| Methanol | 1.4 | 0 | 0.896 | 18.7 |
| Ethanol | 0.18 | 0 | 10.68 | 0.419 |
| Butanol | 0 | 0 | 11.08 | 0 |
| Formic acid | 2.23* | 3.1 | 0 | 0 |
| Acetic acid | 8.36 | 13.78 | 2.16 | 1.89 |
| Propanoic acid | 3.21 | 0 | 0 | 0 |
| Butanoic acid | 7.09 | 11.96 | 1.12 | 0.068 |
| Valeric acid | 3.41 | 2.67 | 0.316 | 0 |
| Caproic acid | 3.94 | 2.34 | 0.06 | 0 |
| Total | 29.82 | 33.85 | 26.312 | 21.077 |

*Required amount of formic acid was amended to make-up 0.5%

Further to that, the experiment was carried out in continuous mode operation of the both the reactors with a HRT of 24 h at a flow rate of 84 ml/h. Current consumption in this case increased to $7.4 \pm 1.08$ A/m$^2$ during stage-1. The cumulative product after 3 days showed the intensification of acetic acid (42.6 g/l) and butyric acid (36.7 g/l) at the expense of other constituents of leachate either completely or partially. Compared to batch mode, the CCE for stage-1 is increased and is about 78%. Subsequently, when the effluent of stage-1 subjected to stage-2, the current consumption recorded as $12.6 \pm 0.9$ A/m$^2$ and $1.63 \pm 0.7$ A/m$^2$ during approach-1 and 2 respectively. Similar to the batch experiments, the intensified acetic and butyric acids were reduced alcohols during stage-2 (Table 3). Butanol (46.93 g/l) production was higher compared to ethanol (21.12 g/l) in continuous mode operation of approach-1, while the methanol was dominant in approach-2 (71.62 g/l). The CCE during stage-2 operation remained more or less similar for approach-1 (91%), while the CCE increased to 61% in approach-2 compared to batch mode.

TABLE 3

Two stage operation of bioreactor in continuous mode using kitchen waste leachate along with $CO_2$ as C-source (Cumulative of 3 days)

|  | Influent VFA (g/l) | Effluent VFA after stage-1 (g/l) | Stage-2/ approach-1, Product formed (g/l) | Stage-2/ approach-2, Product formed (g/l) |
| --- | --- | --- | --- | --- |
| Methanol | 4.2 | 0 | 2.41 | 71.62 |
| Ethanol | 0.54 | 0 | 21.12 | 4.12 |
| Butanol | 0 | 0 | 46.93 | 0 |
| Formic acid | 6.69* | 9.83 | 0 | 0 |
| Acetic acid | 25.08 | 42.6 | 2.87 | 2.87 |
| Propanoic acid | 9.63 | 0 | 0 | 0 |
| Butanoic acid | 21.27 | 36.7 | 2.17 | 0.981 |
| Valeric acid | 10.23 | 8.74 | 0.86 | 0 |
| Caproic acid | 11.82 | 7.62 | 0.18 | 0 |
| Total | 89.46 | 105.49 | 76.54 | 79.57 |

*Required amount of formic acid was amended to make-up 0.5%

Example 4: Leachate from Biomass Waste Along with $CO_2$ as C-Source

In another example, the source of leachate was changed from kitchen waste to biomass waste (VFA: 30.16 g/l; TOC: 41.27 g/l), keeping the bioreactor design and operation same. $CO_2$ was also added at a rate of 15 ml/min and formic acid was maintained at 0.5% by external addition of required quantity. The combination of *Shewanella* sp. MTCC 25020. *Pseudomonas aeruginosa* MTCC 5389, *Geobacter anodireducens*, *Pseudomonas stutzeri* MTCC 25027, was used as biocatalyst during stage-1. Current consumption during stage-1 was observed to be increasing with time and in 5 h of operation, it reached $7.65 \pm 0.7$ A/m$^2$ and sustained afterwards at similar range till 72 h of operation. Similar to the kitchen waste leachate, results showed the intensification of acetic (14.2 g/l) and butyric acids (12.9 g/l) during stage-1 at the expense of other constituents of leachate and $CO_2$ with a CCE of 51% (Table 4).

The effluent from stage-1 operation was used as substrate for both the approaches of stage-2 and no other C-source was provided. Rest of the operating conditions remained same. The combination of Alicaligens sp. MTCC 25022, *Serratia* sp. MTCC 25017, *Lysinibacilhus* sp. MTCC 5666, *Clostridium cellulolyticum* was used as biocatalyst during stage-2. Here also, the current consumption on CA started immediately after start-up during both the approaches of stage-2 and showed a maximum value of $9.68 \pm 0.4$ A/m$^2$ and $1.78 \pm 0.6$ A/m$^2$ respectively. Alcohol production was evident similar to the kitchen waste leachate experiment during both the approaches of stage-2. Approach-1 resulted in the dominant production of butanol (12.19 g/l) and ethanol (10.64), while the approach-2 produced methanol (21.13). During stage-2, about 92% CCE was recorded during approach-1 but the CCE was only 64% during approach-2 due to the non-availability of $H_2/H^+$ in the reactor resulting in the loss of carbon as $CO_2$.

TABLE 4

Two stage operation of bioreactor in batch mode using kitchen waste leachate along with $CO_2$ as C-source

| | Influent VFA (g/l) | Effluent VFA after stage-1 (g/l) | Stage-2/ approach-1, Product formed (g/l) | Stage-2/ approach-2, Product formed (g/l) |
|---|---|---|---|---|
| Methanol | 0.98 | 0 | 0.784 | 21.13 |
| Ethanol | 0.23 | 0 | 10.64 | 3.68 |
| Butanol | 0 | 0 | 12.19 | 0 |
| Formic acid | 1.68* | 3.78 | 0 | 0 |
| Acetic acid | 10.18 | 14.2 | 1.96 | 1.13 |
| Propanoic acid | 6.24 | 0 | 0 | 0 |
| Butanoic acid | 5.61 | 12.9 | 1.16 | 0.73 |
| Valeric acid | 3.68 | 2.61 | 0.398 | 0 |
| Caproic acid | 2.77 | 2.24 | 0.09 | 0 |
| Total | 31.37 | 35.73 | 27.22 | 26.64 |

*Required amount of formic acid was amended to make-up 0.5%

Further to that, the experiment was carried out in continuous mode operation of the both the reactors with a HRT of 24 h at a flow rate of 84 ml/h. Current consumption in this case also increased to 8.3±0.96 A/m² during stage-1. The cumulative product after 3 days showed the intensification of acetic acid (4.28 g/l) and butyric acid (36.68 g/l) at the expense of other constituents of leachate either completely or partially, resulting in CCE of 72%.

Subsequently, the effluent of stage-1 subjected to stage-2 and about 11.3±1.09 A/m2 and 1.82±0.6 A/m² of current consumptions were recorded during approach-1 and 2 respectively. Similar to the batch experiments, the intensified acetic and butyric acids were reduced alcohols during stage-2 (Table 5). Transformation to butanol (45.17 g/l) is higher compared to ethanol (19.86 g/l) during continuous mode operation of approach-1, while the methanol was dominant in approach-2 (69.82 g/l). The CCE during stage-2 operation remained more or less similar for approach-1 (92%), while the CCE increased to 63% in approach-2 compared to batch mode.

TABLE 5

Two stage operation of bioreactor in continuous mode using biomass waste leachate along with $CO_2$ as C-source (Cumulative of 3 days)

| | Influent VFA (g/l) | Effluent VTA after stage-1 (g/l) | Stage-2/ approach-1, Product formed (g/l) | Stage-2/ approach-2, Product formed (g/l) |
|---|---|---|---|---|
| Methanol | 2.94 | 0 | 1.96 | 69.82 |
| Ethanol | 0.69 | 0 | 19.86 | 3.76 |
| Butanol | 0 | 0 | 45.17 | 0 |
| Formic acid | 5.04* | 9.12 | 0 | 0.076 |
| Acetic acid | 30.54 | 41.28 | 1.94 | 1.94 |
| Propanoic acid | 18.72 | 0 | 0 | 0 |
| Butanoic acid | 16.83 | 36.68 | 2.43 | 0.873 |
| Valeric acid | 11.04 | 7.36 | 1.66 | 0 |
| Caproic acid | 8.31 | 5.98 | 0.24 | 0 |
| Total | 94.11 | 100.34 | 73.26 | 76.45 |

*Required amount of formic acid was amended to make-up 0.5%

Example 5: Leachate from Agricultural Waste Along with $CO_2$ as C-Source

In another example, the source of leachate was changed from kitchen waste to agriculture residue (horticulture waste) (VFA: 28.12 g/l; TOC: 38.36 g/l), keeping the bioreactor design and operation same. $CO_2$ was also added at a rate of 15 ml/min and formic acid was maintained at 0.5% by external addition of required quantity. The combination of *Pseudomonas stutzeri* MTCC 25027, *Pseudomonas aeruginosa* MTCC 5389, *Shewanella* sp. MTCC 25020, *Psuedomonas alcaligenes* was used as biocatalyst during stage-1. Current consumption during stage-1 was observed to be increasing with time and in 5 h of operation, it reached 8.43±0.6 A/m2 and sustained afterwards at similar range till 72 h of operation. Similar to the kitchen waste leachate, results showed the intensification of acetic (13.68 g/l) and butyric acids (11.42 g/l) during stage-1 at the expense of other constituents of leachate and $CO_2$ with a CCE of 49% (Table 6).

The effluent from stage-1 operation was used as substrate for both the approaches of stage-2 and no other C-source was provided. Rest of the operating conditions remained same. The combination of *Pseudomonas putida* MTCC 5387, *Pseudomonas aeruginosa* strain MTCC 5388, *Geobacter sufirreducens*, *Serratia* sp. MTCC 25017, *Clostridium celulovorans*, was used as biocatalyst during stage-2. Here also, the current consumption on CA started immediately after start-up during both the approaches of stage-2 and showed a maximum value of 10.42±0.38 A/m2 and 2.36±0.6 A/m² respectively. Alcohol production was evident similar to the agricultural waste leachate experiment during both the approaches of stage-2. Approach-1 resulted in the dominant production of butanol (10.31 g/l) and ethanol (9.42), while the approach-2 produced methanol (17.18). During stage-2, about 94% CCE was recorded during approach-1 but the CCE was only 58% during approach-2 due to the non-availability of $H_2/H^+$ in the reactor resulting in the loss of carbon as $CO_2$.

TABLE 6

Two stage operation of bioreactor in batch mode using agriculture waste leachate along with $CO_2$ as C-source

| | Influent VFA (g/l) | Effluent VFA after stage-1 (g/l) | Stage-2/ approach-1, Product formed (g/l) | Stage-2/ approach-2, Product formed (g/l) |
|---|---|---|---|---|
| Methanol | 0.63 | 0 | 0.662 | 17.18 |
| Ethanol | 0.41 | 0 | 9.42 | 2.82 |
| Butanol | 0 | 0 | 10.31 | 0 |
| Formic acid | 1.34* | 3.78 | 0 | 0 |
| Acetic acid | 8.87 | 13.68 | 2.84 | 4.18 |
| Propanoic acid | 4.26 | 0 | 0 | 0 |
| Butanoic acid | 5.18 | 11.42 | 1.67 | 1.07 |
| Valeric acid | 2.64 | 1.63 | 0.43 | 0 |
| Caproic acid | 3.12 | 0 | 0 | 0 |
| Total | 26.45 | 30.51 | 25.332 | 25.25 |

*Required amount of formic acid was amended to make-up 0.5%

Further to that, the experiment was carried out in continuous mode operation of the both the reactors with a HRT of 24 h at a flow rate of 84 ml/h. Current consumption in this case also increased to 7.16±0.6 A/m² during stage-1. The cumulative product after 3 days showed the intensification of acetic acid (39.36 g/l) and butyric acid (31.42 g/l) at the expense of other constituents of leachate either completely or partially, resulting in CCE of 68%.

Subsequently, the effluent of stage-1 subjected to stage-2 and about 12.11±0.93 A/m2 and 1.78±0.34 A/m² of current consumptions were recorded during approach-1 and 2 respectively. Similar to the batch experiments, the intensified acetic and butyric acids were reduced alcohols during stage-2 (Table 7). Transformation to butanol (38.18 g/l) is higher compared to ethanol (29.32 g/l) during continuous mode operation of approach-1, while the methanol was dominant in approach-2 (73.16 g/l). The CCE during stage-2 operation remained more or less similar for approach-1 (94%), while the CCE increased to 64% in approach-2 compared to batch mode.

TABLE 7

Two stage operation of bioreactor in continuous mode using agriculture waste leachate along with $CO_2$ as C-source (Cumulative of 3 days)

| | Influent VFA (g/l) | Effluent VFA after stage-1 (g/l) | Stage-2/ approach-1, Product formed (g/l) | Stage-2/ approach-2, Product formed (g/l) |
|---|---|---|---|---|
| Methanol | 0.63 | 0 | 2.04 | 73.16 |
| Ethanol | 0.41 | 0 | 29.32 | 3.76 |
| Butanol | 0 | 0 | 38.18 | 0 |
| Formic acid | 1.34* | 10.18 | 0 | 0 |
| Acetic acid | 8.87 | 39.36 | 1.08 | 2.96 |
| Propanoic acid | 4.26 | 0 | 0 | 0 |
| Butanoic acid | 5.18 | 31.42 | 1.26 | 0 |
| Valeric acid | 2.64 | 6.66 | 0.98 | 0 |
| Caproic acid | 3.12 | 6.04 | 0 | 0 |
| Total | 26.45 | 93.66 | 72.86 | 79.88 |

*Required amount of formic acid was amended to make-up 0.5%

Example 6-10: Different Electrode Materials, Microbes and Power Supply Mode Combinations Keeping C-Source Constant i.e., Leachate from Kitchen Waste Along with $CO_2$ In examples 5 to 9, all the experiments were carried out using leachate from kitchen waste (VFA: 28.24 g/l; TOC: 34.61 g/l) along with $CO_2$ as C-source (15 ml/min) and formic acid was maintained at 0.5% by external addition of required quantity. However, the working and counter electrodes for both stage 1 and stage 2 were varied as well as the microbial blend used and the power supply mode (potentiostat or galvanostat) was changed (Table 8). All these experiments also showed current consumption pattern in similar lines. However, the product profile varied slightly with the microbe nature. The example 8 and Example 9, where *Propinibacterium* Sp. was used, propionc acid production was also dominantly observed along with acetic acid which is not the case with other experiments. (Table 9-13).

The effluent from stage-1 operation was made as substrate for stage-2 of both the approaches and no other C-source was provided for stage-2 operation. Rest of the operating conditions was varied between each experimental set-up as described in Table 8. All the experimental combinations (Example 6-10) showed very good current consumption for approach-1 and lower current consumption for approach-2, similar to the example-1 indicating the role of presence of H2/H+. Alcohol production was observed during both the approaches of stage-2 but approach-1 resulted in the dominant production of butanol and ethanol, while the approach-2 produced methanol. In situ generation of H2/H+ is the major reason behind the variation in alcohol composition. The average CCE lies in the range of 44-52% during stage-1, while it is more than 90% during approach-1 of stage-2 irrespective of the experimental combinations. The CCE was only 50% during approach-2 of stage-2 due to the non-availability of HJH in the reactor resulting in the loss of carbon as $CO_2$.

TABLE 8

Different experimental combinations studied using kitchen waste leachate along with CO2 as C-source

| | Example 5 | Example 6 | Example 7 | Example 8 | Example 9 |
|---|---|---|---|---|---|
| Stage-1 | | | | | |
| Working electrode | Carbon brush | ACC | Graphite Felt | Graphite Felt | Carbon paper |
| Counter electrode | Graphite rod modified with CNT | Graphite rod modified with Graphene | Graphite rod modified with Charcoal | Graphite rod modified with CNT | Graphite rod modified with NiO |
| Microbes | *Enterobacter aerogenes* MTCC 25016, *Pseudomonas fragi* MTCC 25025, *Pseudomonas aeruginosa* MTCC 5389, *Shewanella* sp. MTCC 25020 | *Clostridium ljungdahlii*, *Pseudomonas stutzeri* MTCC 25027, *Shewanella* sp. MTCC 25020 | *Enterobacter aerogenes* MTCC 25016, *Pseudomonas aeruginosa* MTCC 5389, *Shewanella* sp. MTCC 25020 | *Enterobacter aerogenes* MTCC 25016, *Pseudomonas aeruginosa* MTCC 5389, *Shewanella* sp. MTCC 25020 | *Shewanella* sp. MTCC 25020, *Pseudomonas fragi* MTCC 25025, *Pseudomonas stutzeri* MTCC 25027, *Enterobacter aerogenes* MTCC 25016 |
| Power supply mode | Potentiostat mode 2 V | Potentiostat mode 3 V | Galvanostat mode 75 mA/m2 | Potentiostat mode 4 V | Galvanostat mode 100 mA/m2 |
| Stage-2 | | | | | |
| Working electrode | Graphite rod modified with CNT | Carbon plate modified with graphene | Carbon plate modified with CNT and activated charcoal | Graphite rod modified with activated charcoal | Graphite rod graphene |

TABLE 8-continued

Different experimental combinations studied using kitchen waste leachate along with CO2 as C-source

|  | Example 5 | Example 6 | Example 7 | Example 8 | Example 9 |
|---|---|---|---|---|---|
| Counter electrode (Approach 1) | Graphite plate modified with $Co_9S_8$ | Graphite plate modified with ZnO nano particles | Graphite felt modified with $Si/TiO_2$ nanowires | ACC modified with Ni/Fe LDH (layered double hydroxide) | Carbon brush modified with FTO/NiO |
| Counter electrode (Approach 2) | Graphite plate | Graphite plate | Graphite felt | ACC | Carbon brush |
| Electron shuttler | Neutral red | Methylene blue | Neutral red and NiO | Neutral red | AQDS |
| Microbes | Pseudomonas aeruginosa strain MTCC 5388, Serratia sp. MTCC 25017, Alicaligens sp. MTCC 25022 | Pseudomonas aeruginosa strain MTCC 5388, Lysinibacillus sp. MTCC 5666, Pseudomonas putida MTCC 5387, Clostridium butyricum | Clostridium carboxidivorans, Pseudomonas putida MTCC 5387, Alicaligens sp. MTCC 25022, Clostridium beijerinckii | Pseudomonas aeruginosa strain MTCC 5388, Serratia sp. MTCC 25017, Clostridium beijerinckii, Lysinibacillus sp. MTCC 5666 | Serratia sp. MTCC 25017, Clostridium carboxidivorans, Lysinibacillus sp. MTCC 5666, |
| Power supply mode | Potentiostat mode 3 V | Potentiostat mode 4 V | Galvanostat mode 100 mA/m2 | Galvanostat mode 250 mA/m2 | Potentiostat mode 6 V |

TABLE 9

Two stage operation of bioreactor in batch mode using kitchen waste leachate along with $CO_2$ as C-source with experimental combinations of Example 5

|  | Influent VFA/alcohols (g/l) | Effluent VFA/alcohols after stage-1 (g/l) | Stage-2/approach-1, Product formed (g/l) | Stage-2/approach-2, Product formed (g/l) |
|---|---|---|---|---|
| Methanol | 1.4 | 0 | 0.896 | 19.2 |
| Ethanol | 0.18 | 0 | 9.63 | 0.212 |
| Butanol | 0 | 0 | 11.48 | 0 |
| Formic acid | 2.23* | 3.4 | 0 | 0 |
| Acetic acid | 8.36 | 14.62 | 3.34 | 2.06 |
| Propanoic acid | 3.21 | 0 | 0 | 0 |
| Butanoic acid | 7.09 | 12.34 | 0.98 | 0 |
| Valeric acid | 3.41 | 1.16 | 0.412 | 0 |
| Caproic acid | 3.94 | 0.98 | 0.004 | 0 |
| Total | 29.82 | 32.50 | 26.742 | 21.472 |

*Required amount of formic acid was amended to make-up 0.5%

TABLE 10

Two stage operation of bioreactor in batch mode using kitchen waste leachate along with $CO_2$ as C-source with experimental combinations of Example 6

|  | Influent VFA alcohols (g/l) | Effluent VFA alcohols after stage-1 (g/l) | Stage-2/approach-1, Product formed (g/l) | Stage-2/approach-2, Product formed (g/D) |
|---|---|---|---|---|
| Methanol | 1.4 | 0 | 1.023 | 16.35 |
| Ethanol | 0.18 | 0 | 11.22 | 0.868 |
| Butanol | 0 | 0 | 10.68 | 0 |
| Formic acid | 2.23* | 2.21 | 0 | 0 |
| Acetic acid | 8.36 | 12.93 | 2.34 | 1.91 |
| Propanoic acid | 3.21 | 0 | 0 | 0 |
| Butanoic acid | 7.09 | 13.21 | 1.31 | 0 |
| Valeric acid | 3.41 | 0.67 | 0.042 | 0 |
| Caproic acid | 3.94 | 1.41 | 0 | 0 |
| Total | 29.82 | 30.43 | 26.615 | 19.128 |

*Required amount of formic acid was amended to make-up 0.5%

TABLE 11

Two stage operation of bioreactor in batch mode using kitchen waste leachate along with $CO_2$ as C-source with experimental combinations of Example 7

|  | Influent VFA alcohols (g/l) | Effluent VFA alcohols after stage-1 (g/l) | Stage-2/approach-1, Product formed (g/l) | Stage-2/approach-2, Product formed (g/l) |
|---|---|---|---|---|
| Methanol | 1.4 | 0 | 0.414 | 19.86 |
| Ethanol | 0.18 | 0 | 8.36 | 0.061 |
| Butanol | 0 | 0 | 15.41 | 0.216 |
| Formic acid | 2.23* | 2.86 | 0 | 0 |
| Acetic acid | 8.36 | 8.61 | 2.34 | 2.03 |
| Propanoic acid | 3.21 | 6.42 | 0.621 | 0.122 |
| Butanoic acid | 7.09 | 14.13 | 0.941 | 0 |
| Valeric acid | 3.41 | 2.12 | 0.068 | 0 |
| Caproic acid | 3.94 | 0.34 | 0 | 0 |
| Total | 29.82 | 34.48 | 28.154 | 22.289 |

*Required amount of formic acid was amended to make-up 0.5%

TABLE 12

Two stage operation of bioreaetor in batch mode using kitchen waste leaehate along with $CO_2$ as C-source with experimental combinations of Example 8

| | Influent VFA alcohols (g/l) | Effluent VFA alcohols after stage-1 (g/l) | Stage-2/ approach-1, Product formed (g/l) | Stage-2/ approach-2, Product formed (g/l) |
|---|---|---|---|---|
| Methanol | 1.4 | 0 | 0.623 | 18.24 |
| Ethanol | 0.18 | 0 | 7.45 | 0.047 |
| Butanol | 0 | 0 | 13.86 | 0.188 |
| Formic acid | 2.23* | 2.72 | 0 | 0 |
| Acetic acid | 8.36 | 6.96 | 2.86 | 1.641 |
| Propanoic acid | 3.21 | 8.16 | 0.787 | 0.063 |
| Butanoic acid | 7.09 | 12.88 | 0.612 | 0 |
| Valeric acid | 3.41 | 1.97 | 0 | 0 |
| Caproic acid | 3.94 | 1.62 | 0 | 0 |
| Total | 29.82 | 34.31 | 26.192 | 20.179 |

*Required amount of formic acid was amended to make-up 0.5%

TABLE 13

Two stage operation of bioreactor in batch mode using kitehen waste leachate along with $CO_2$ as C-source with experimental combinations of Example 9

| | Influent VFA alcohols (g/l) | Effluent VFA alcohols after stage-1 (g/l) | Stage-2/ approach-1, Product formed (g/l) | Stage-2/ approach-2, Product formed (g/L) |
|---|---|---|---|---|
| Methanol | 1.4 | 0 | 0.163 | 20.36 |
| Ethanol | 0.18 | 0 | 12.68 | 0 |
| Butanol | 0 | 0 | 9.64 | 0 |
| Formic acid | 2.23* | 3.2 | 0 | 0 |
| Acetic acid | 8.36 | 10.08 | 3.12 | 3.412 |
| Propanoic acid | 3.21 | 0 | 0 | 0 |
| Butanoic acid | 7.09 | 15.16 | 1.08 | 1.126 |
| Valeric acid | 3.41 | 1.92 | 0.621 | 0 |
| Caproic acid | 3.94 | 2.04 | 0 | 0 |
| Total | 29.82 | 32.40 | 27.304 | 24.898 |

*Required amount of formic acid was amended to make-up 0.5%

The results obtained from this study will represent a highly efficient, cost-effective process for the conversion of VFA rich organic waste to drop-in fuels. Hybrid process of biocatalyst activities along with electrochemical reactions, in situ $H_2/H^+$ generation during stage-2 and the syntrophic association of different groups of bacteria such as acid producing bacteria, chemoautotrophic bacteria, homoacetogens, and EAB are the key element of the process.

Whereas the principal inventive concept has been described in this provisional patent application, the invention will be fully and particularly described in the complete patent application pursuant hereto.

*Pseudomonas stutzeri* MTCC 25027 is a Gram-negative, rod-shaped, non-spore-forming bacterium, positive for both the catalase and oxidase tests and is electroactive in nature. *Pseudomonas fragi* MTCC 25025 is a Gram-negative, rod-shaped, non-spore-forming electroactive bacterium, oxidase test-Positive, indole negative, methyl red negative, Voges-Proskauer test negative and citrate positive. *Pseudomonas aeruginosa* MTCC 5389 is a Gram-negative, rod-shaped, non-spore-forming electroactive bacterium, oxidase test-Positive, indole negative, methyl red negative, Voges-Proskauer test Positive and citrate positive. *Enterobacter aerogenes* MTCC 25016 is a Gram-negative motile, oxidase negative, catalase positive, citrate positive, indole negative, Methyl Red-negative rod-shaped electroactive bacterium. *Shewanella* sp. MTCC 25020 is a facultatively anaerobic, Gram-negative rod-shaped bacteria, motile by polar flagella, extracellular electron acceptor. *Pseudomonas aeruginosa* MTCC 5388 is a Gram-negative, rod-shaped, non-spore-forming electroactive bacterium, oxidase test-Positive, indole Positive, methyl red. negative, Voges-Proskauer test: Positive and citrate positive. *Pseudomonas putida* MTCC 5387 is a Gram-negative, rod-shaped, catalase positive, cytochrome C oxidase positive, lecithinase/alpha: negative; casein hydrolysis: negative, D-trehalose: negative, Poly-&-hydroxybutyric acid: positive, extracellular electron acceptor. *Alicaligens* sp. MTCC 25022 is a Gram-negative, aerobic, rod-shaped bacteria, extracellular electron acceptor. *Serratia* sp. MTCC 25017 is a rod-shaped, Gram-negative bacteria, facultative anaerobe, high catalase-producing, electro-active bacteria, citrate positive, flagella positive, gelatin hydrolysis positive, indole negative, Motility Positive, Methyl Red: Negative, Nitrate Reduction: Positive, Oxidase Negative, rod shaped, spore negative, urease positive, Voges Proskauer: positive. *Lysinibacillus* sp. MTCC 5666 is a Gram-positive, motile with rod-shaped cells that produce endospores of ellipsoidal or spherical shape; positive for oxidase and catalase tests while negative for indole and $H_2S$ production.

The invention claimed is:

1. A bio-assisted process for production of drop-in fuels from $CO_2$ and a volatile fatty acid rich source, said process comprising:
   (a) providing a first electrochemical system comprising at least one working electrode, at least one counter electrode, and a medium inoculated with selectively enriched electro-active bacteria selected from the group consisting of *Geobacter anodireducens*, *Clostridium ljungdahlii*, *Acetobacterium woodii*, *Sporomusa acidovorans*, *Propionibacterium acidifaciens*, *Acetobacterium carbinolicum*, *Pseudomonas stutzeri* MTCC 25027, *Pseudomonas fragi* MTCC 25025, *Pseudomonas aeruginosa* MTCC 5389, *Psuedomonas alcaligenes*, *Schewanella putrefaciens*, *Clostridium aciditolerans*, *Enterobacter aerogenes* MTCC 25016, *Shewanella* sp. MTCC 25020, and combinations thereof;
   (b) providing feedstock to the first electrochemical system of step (a), wherein the feedstock comprises $CO_2$ with the volatile fatty acid rich source;
   (c) intensifying carboxylic acids in the feedstock of step (b) to obtain an effluent comprising intensified carboxylic acids;
   (d) providing a second electrochemical system comprising at least one working electrode, at least one counter electrode, and a medium inoculated with selectively enriched electro-active bacteria selected from the group consisting of *Sporomusa ovate*, *Clostridium acetobutylicum*, *Clostridium butyricum*, *Clostridium acidurici*, *Pseudomonas aeruginosa* MTCC 5388, *Pseudomonas putida* MTCC 5387, *Clostridium carboxidivorans*, *Clostridium beijerinckii*, *Schewanella oneidensis*, *Geobacter sdfurreducens*, *Clostridium cellutolyticum*, *Clostridium cellulosi*, *Clostridium cellulovorans*, *Alicaligens* sp. MTCC 25022, *Serratia* sp. MTCC 25017, *Lysinibacillus* sp. MTCC 5666, and combinations thereof; and
   (e) reducing the intensified carboxylic acids of step (c) in the second electrochemical system to obtain the drop-in fuels;

wherein the working electrode of the first electrochemical system is composed of a material selected from the group consisting of graphite plate, carbon brush, carbon paper, graphite felt, activated carbon cloth, and combinations thereof;

wherein the counter electrode of the first electrochemical system is modified with a material selected from the group consisting of carbon nanotube (CNT), graphene, charcoal, activated carbon, stainless steel (SS) mesh, nickel oxide, zinc oxide, and iron oxide;

wherein the volatile fatty acid rich source comprises at least 0.5% formic acid, provided that if the formic acid is not already present in the feedstock the feedstock is supplemented with at least 0.5% formic acid;

wherein the working electrode of the second electrochemical system is composed of a material selected from the group consisting of graphite plate, graphite rod, carbon brush, carbon paper, carbon plate, graphite felt, activated carbon cloth, and combinations thereof; and wherein the counter electrode of the second electrochemical system is modified with a material selected from the group consisting of CNT, $Co_9S_8$, graphene, FTO/NiO, Ni/Fe layered double hydroxide, $Si/TiO_2$ nanowires, charcoal, activated carbon, nickel oxide, zinc oxide, and iron oxide; and wherein the drop-in fuels are selected form the group consisting of methanol, ethanol, butanol, acetic acid, propanoic acid, butanoic acid, valeric acid, and caproic acid.

2. The bio-assisted process as claimed in claim 1, wherein the first electrochemical system is operated at a temperature ranging from 20° C. to 50° C.

3. The bio-assisted process as claimed in claim 1, wherein the first electrochemical system is operated at a pH ranging from 6.5 to 9.0.

4. The bio-assisted process as claimed in claim 1, wherein the first electrochemical system is operated at an applied potential ranging from 1V to 4V.

5. The bio-assisted process as claimed in claim 1, wherein the working electrode of the second electrochemical system is modified with a material selected from the group consisting of CNT, graphene, activated charcoal, noble metal, composite of Zr or Ti or Cd or Fe, metal-free alloy, metal carbide, phosphide, and nickel oxide, zinc oxide, iron oxide, metal-phosphorous alloy, metal-sulfur alloy, metal organic framework, and combinations thereof.

6. The bio-assisted process as claimed in claim 1, wherein the carboxylic acid in step (c) has a length ranging from C2 to C6.

7. The bio-assisted process as claimed in claim 1, wherein the second electrochemical system is operated at a temperature ranging from 20° C. to 50° C.

8. The bio-assisted process as claimed in claim 1, wherein the second electrochemical system is operated at a pH ranging from 4.0 to 6.0.

9. The bio-assisted process as claimed in claim 1, wherein the second electrochemical system is operated at an applied potential ranging from 2V to 6V.

10. The bio-assisted process as claimed in claim 1, wherein the volatile fatty acid rich source is selected from the group consisting of kitchen waste, biomass waste, agricultural waste, biodegradable municipal waste, lignocellulosic waste, and de-oiled algal cake.

11. The bio-assisted process as claimed in claim 1, wherein the reduction of carboxylic acids in step (e) is carried out in presence of a redox shuttler selected from the group consisting of neutral red, methylene blue, phenazine derivative, iron based metal complex, nickel based metal complex, zinc based metal complex, anthraquinone-2,6-disulfonate (AQDS), and combinations thereof.

* * * * *